United States Patent [19]

Yamatsu et al.

[11] Patent Number: 4,576,963

[45] Date of Patent: Mar. 18, 1986

[54] POLYPRENYL COMPOUNDS, PROCESS FOR THE PRODUCTION THEREOF AND MEDICINES CONTAINING SAME

[75] Inventors: Isao Yamatsu, Ushikumachi; Shinya Abe, Kukisakimura; Yuichi Inai, Tokyo; Takeshi Suzuki, Ushikumachi; Kensaku Kinoshita, Abiko; Mannen Mishima, Yatabemachi; Yoshinori Katoh, Misato; Seiichi Kobayashi, Tsuchiura; Manabu Murakami, Toyosatomachi; Kouzi Yamada, Toride, all of Japan

[73] Assignee: Eisai Co., Ltd., Tokyo, Japan

[21] Appl. No.: 609,664

[22] Filed: May 14, 1984

Related U.S. Application Data

[62] Division of Ser. No. 396,184, Jul. 8, 1982, Pat. No. 4,455,316.

[30] Foreign Application Priority Data

Jul. 23, 1981 [JP] Japan .................................. 56-114371

[51] Int. Cl.[4] .................. A61K 31/235; C07C 69/612
[52] U.S. Cl. ..................................... 514/532; 560/113
[58] Field of Search ....................... 560/43, 48, 66, 67, 560/113; 424/308, 309; 514/532

[56] References Cited

U.S. PATENT DOCUMENTS 4,059,641  11/1977  Mishima ............................... 560/113
4,192,953  3/1980  Mishima ............................... 560/113

OTHER PUBLICATIONS

Opdyke, D., *Chemical Abstracts*, 86:145738g, (1977).
Proksch, P. et al., *Chemical Abstracts*, 93:53738y, (1980).

*Primary Examiner*—Natalie Trousof
*Assistant Examiner*—Bruce D. Gray
*Attorney, Agent, or Firm*—Flynn, Thiel, Boutell & Tanis

[57] ABSTRACT

Non-steroidal, anti-inflammatory drugs are disclosed which are polyprenyl alcohol esters of indolyl lower carboxylic acids, phenyl lower carboxylic acids, acetyl salicylic acid, anthranilic acid and derivatives thereof.

6 Claims, No Drawings

POLYPRENYL COMPOUNDS, PROCESS FOR THE PRODUCTION THEREOF AND MEDICINES CONTAINING SAME

This is a division of application Ser. No. 396 184, filed July 8, 1982, now U.S. Pat. No. 4,455,316.

The present invention relates to new polyprenyl compounds having excellent medicinal effects, processes for the production thereof and pharmaceutical compositions containing same.

More particularly, the present invention relates to polyprenyl compounds of the general formula:

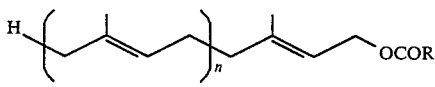

wherein R represents:
(a) a group of the formula:

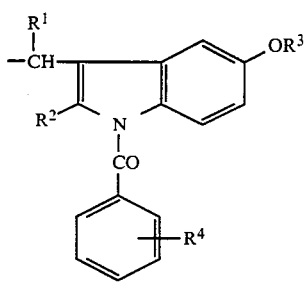

in which $R^1$ and $R^2$ each represent a hydrogen atom or a lower alkyl group, $R^3$ represents a lower alkyl group and $R^4$ represents a hydrogen atom, a halogen atom or a lower alkyl group,
(b) a group of the formula:

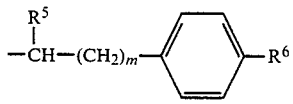

in which $R^5$ represents a hydrogen atom or a lower alkyl group, $R^6$ represents a lower alkyl group and m represents an integer of 0 or 1,
(c) a group of the formula:

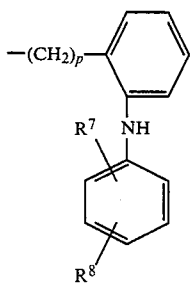

in which $R^7$ and $R^8$ are the same or different and each represent a hydrogen atom, a lower alkyl group, a halogen atom or a trifluoromethyl group and p represents an integer of 0 or 1, or
(d) a group of the formula:

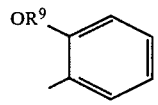

in which $R^9$ represents a hydrogen atom or an acetyl group, and n represents an integer of 1 to 3, processes for the production thereof and pharmaceutical compositions containing same.

The term "lower alkyl group" in the definition of $R^1$, $R^2$, $R^3$, $R^4$, $R^5$, $R^6$, $R^7$ and $R^8$ refers to a straight-chain or branched alkyl group having 1 to 6 carbon atoms, such as methyl, ethyl, n-propyl, isopropyl, isobutyl, 1-methyl-propyl, tert-butyl, n-pentyl, 1-ethylpropyl, isoamyl or n-hexyl group. The term "halogen atom" refers to chlorine, bromine, iodine or fluorine.

The polyprenyl alcohol compounds provided by the present invention are new compounds which have not yet been disclosed in the literature. They have a remarkable anti-inflammatory effect and only a low toxicity.

Anti-inflammatory drugs can roughly be classified into four groups, i.e. steroid hormones, non-steroidal anti-inflammatory drugs, anti-inflammatory enzymes and immunosuppressants. Among them, the non-steroidal anti-inflammatory drugs are most important. Recently, studies have been made on the development of non-steroidal anti-inflammatory drugs all over the world.

Compounds widely used as non-steroidal anti-inflammatory drugs are indoleacetic acids, such as Indomethacin; phenylacetic acids, such as Ibufenac and Ibuprofen; salicylic acid compounds, such as aspirin, salicylic acid per se and salicylosalicylic acid; anthranilic acids, such as mefenamic acid and flufenamic acid; pyrazolinediones, such as phenylbutazone, oxyphenylbutazone and ketophenylbutazone; and basic compounds such as Benzydamine, Mepirizole and Tinoridine.

However, these non-steroidal anti-inflammatory drugs have many clinical problems. The most serious problems are the side-effects on the gastrointestinal tract and kidneys. Particularly, Indomethacin, which is a typical indoleacetic acid compound having the strongest anti-inflammatory effect among the non-steroidal anti-inflammatory drugs now available on the market, is a non-steroidal anti-inflammatory drug of first choice and it is used also for the treatment of rheumatism. Although Indomethacin has a high therapeutic value, it also has serious side effects on the stomach, intestines, central nervous system and kidneys. These side effects hinder the practical use of the non-steroidal anti-inflammatory drugs. These problems of side effects are very important, because continuous administration of the drug for a long period of time is required to treat patients suffering from rheumatism and the anti-inflammatory drug should be administered in a large dose.

The therapeutic effects and side effects of non-steroidal anti-inflammatory drugs vary from patient to patient. Therefore, various types of drugs are required.

In view of these circumstances, the development of new anti-inflammatory drugs having long-lasting therapeutic effects, but insignificant side effects, has been demanded.

After intensive investigations made for a long period of time, for the purpose of developing anti-inflammatory drugs having a long-lasting therapeutic effect, but only insignificant side effects under these circumstances, the inventors have discovered that the compounds of the present invention satisfy these requirements. The present invention has been completed on the basis of this discovery.

More particularly, the inventors have found that polyprenyl compounds of the general formula:

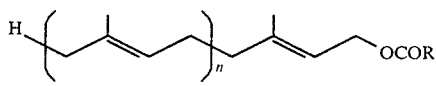

wherein R represents:
(a) a group of the formula:

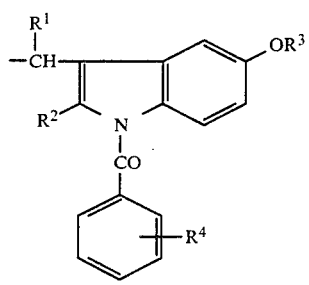

in which $R^1$ and $R^2$ each represent hydrogen or lower alkyl, $R^3$ represents lower alkyl, and $R^4$ represents hydrogen, halogen or lower alkyl,
(b) a group of the formula:

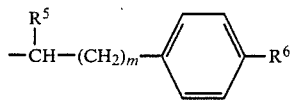

in which $R^5$ represents hydrogen or lower alkyl, $R^6$ represents lower alkyl and m represents ann integer of 0 (zero) or 1,
(c) a group of the formula:

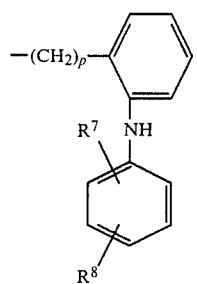

in which $R^7$ and $R^8$ are the same or different and each represent hydrogen, lower alkyl, halogen or trifluoromethyl and p represents an integer of 0 or 1, or
(d) a group of the formula:

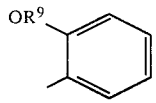

in which $R^9$ represents hydrogen or acetyl, and n represents an integer of 1 to 3, act as anti-inflammatory drugs having a long-lasting anti-inflammatory effect and only insignificant side effects on the stomach, intestines, central nervous system and kidneys.

An object of the present invention is to provide new compounds having excellent anti-inflammatory effects.

Another object of the present invention is to provide new compounds having high safety and remarkably reduced side effects on the gastrointestinal tract and kidneys, which side effects have been the drawbacks of non-steroidal anti-inflammatory drugs used heretofore.

Still another object of the present invention is to provide new compounds having long-lasting anti-inflammatory activity.

A further object of the present invention is to provide processes for producing said compounds having excellent anti-inflammatory effects.

An additional object of the present invention is to provide new anti-inflammatory drugs having long-lasting anti-inflammatory therapeutic effects and only insignificant side effects.

It is considered that various processes can be employed for the production of the compounds of the present invention, since the compounds are polyprenyl alcohol esters. Among them, typical processes will be shown below:

Preparative process 1

The terminal hydroxyl group of a polyprenyl alcohol of the general formula:

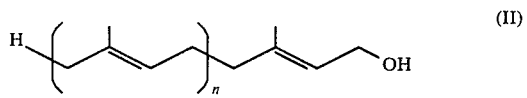

wherein n represents an integer of 1–3, is esterified by a conventional method to obtain the intended product of formula (I).

A typical esterification process of this kind comprises reacting polyprenyl alcohol of the above general formula (II) with:
(a) a compound of the general formula:

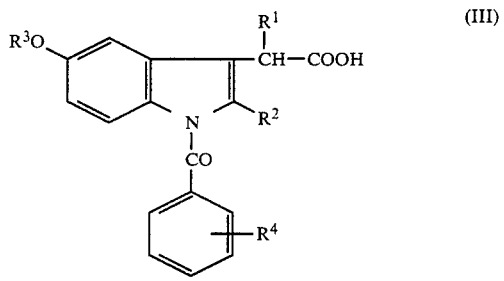

wherein $R^1$ and $R^2$ each represent hydrogen or lower alkyl, $R^3$ represents lower alkyl and $R^4$ represents hydrogen, halogen or lower alkyl,
(b) a compound of the general formula:

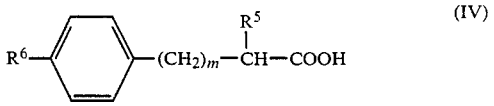

wherein R[5] represents hydrogen or lower alkyl, R[6] represents lower alkyl and m represents an integer of 0 or 1, (c) a compound of the general formula:

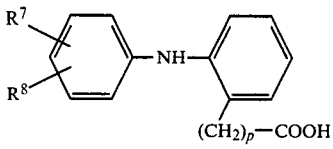 (V)

wherein R[7] and R[8] are the same or different and each represent hydrogen, lower alkyl, halogen or trifluoromethyl and p represents an integer of 0 or 1, or (d) a compound of the general formula:

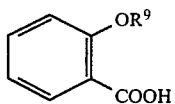 (VI)

wherein R[9] represents hydrogen or acetyl, or a reactive derivative of any of above compounds (III)–(VI) to obtain the intended ester of formula (I).

The most preferred conventional process comprises reacting a halide of one of the above-mentioned carboxylic acid compounds of the formula (III), (IV), (V) or (VI) with the compound (II) to readily obtain the corresponding compound of formula (I) of the present invention. In this reaction, for example, tetrahydrofuran, dioxane, dimethylformamide or chloroform can be used as a solvent. If necessary, an acid scavenger such as triethylamine, potassium carbonate or sodium carbonate is used to obtain better results.

Preparative process 2

A compound of the general formula:

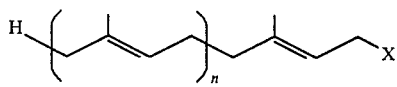 (VII)

wherein n represents an integer of 1–3 and X represents a halogen atom, is reacted with a compound of the formula (III), (IV), (V) or (VI) in the presence of an acid scavenger by a conventional method to readily obtain the intended product of the formula (I).

Typical compounds of the present invention will be set forth below, which by no means limit the compounds of the invention:

2-[(2,6-dichlorophenyl)amino]phenylacetic acid 3,7,11,15-tetramethyl-2,6,10,14-hexadecatetraenyl ester,
2-[(2,6-dichlorophenyl)amino]phenylacetic acid 3,7,11-trimethyl-2,6,10-dodecatrienyl ester,
2-[(2,6-dichlorophenyl)amino]phenylacetic acid 3,7-dimethyl-2,6-octadienyl ester,
2-(4-isobutylphenyl)propionic acid 3,7,11,15-tetramethyl-2,6,10,14-hexadecatetraenyl ester,
2-(4-isobutylphenyl)propionic acid 3,7-dimethyl-2,6-octadienyl ester,
2-(4-isobutylphenyl)propionic acid 3,7,11-trimethyl-2,6,10-dodecatrienyl ester,
acetylsalicylic acid 3,7,11,15-tetramethyl-2,6,10,14-hexadecatetraenyl ester,
acetylsalicylic acid 3,7,11-trimethyl-2,6,10-dodecatrienyl ester,
acetylsalicylic acid 3,7-dimethyl-2,6-octadienyl ester,
1-(p-chlorobenzoyl)-2-methyl-5-methoxy-3-indolylacetic acid 3,7-dimethyl-2,6-octadienyl ester,
1-(p-chlorobenzoyl)-2-methyl-5-methoxy-3-indolylacetic acid 3,7,11,15-tetramethyl-2,6,10,14-hexadecatetraenyl ester,
1-(p-chlorobenzoyl)-2-methyl-5-methoxy-3-indolylacetic acid 3,7,11-trimethyl-2,6,10-dodecatrienyl ester,
N-(2,3-xylyl)anthranilic acid 3,7,11,15-tetramethyl-2,6,10,14-hexadecatetraenyl ester,
N-(2,3-xylyl)anthranilic acid 3,7,11-trimethyl-2,6,10-dodecatrienyl ester,
N-(2,3-xylyl)anthranilic acid 3,7-dimethyl-2,6-octadienyl ester,
N-(3'-trifluoromethylphenyl)anthranilic acid 3,7-dimethyl-2,6-octadienyl ester,
N-(3'-trifluoromethylphenyl)anthranilic acid 3,7,11-trimethyl-2,6,10-dodecatrienyl ester,
N-(3'-trifluoromethylphenyl)anthranilic acid 3,7,11,15-tetramethyl-2,6,10,14-hexadecatetraenyl ester,
(1-benzoyl-2-methyl-5-methoxy-3-indolyl)acetic acid 3,7,11,15-tetramethyl-2,6,10,14-hexadecatetraenyl ester,
(1-benzoyl-2-methyl-5-methoxy-3-indolyl)acetic acid 3,7,11-trimethyl-2,6,10-dodecatrienyl ester,
2-[1-(p-chlorobenzoyl)-2-methyl-5-methoxy-3-indolyl]propionic acid 3,7-dimethyl-2,6-octadienyl ester,
2-[1-(p-chlorobenzoyl)-2-methyl-5-methoxy-3-indolyl]propionic acid 3,7,11,15-tetramethyl-2,6,10,14-hexadecatetraenyl ester,
2-[1-(p-chlorobenzoyl)-2-methyl-5-methoxy-3-indolyl]propionic acid 3,7,11-trimethyl-2,6,10-dodecatrienyl ester,
1-(m-chlorobenzoyl)-2-methyl-5-ethoxy-3-indolylacetic acid 3,7,11,15-tetramethyl-2,6,10,14-hexadecatetraenyl ester,
1-(m-chlorobenzoyl)-2-methyl-5-ethoxy-3-indolylacetic acid 3,7,11-trimethyl-2,6,10-dodecatrienyl ester,
1-(p-methylbenzoyl)-2-methyl-5-methoxy-3-indolylacetic acid 3,7-dimethyl-2,6-octadienyl ester, and
1-(p-methylbenzoyl)-2-methyl-5-ethoxy-3-indolylacetic acid 3,7,11-trimethyl-2,6,10-dodecatrienyl ester.

For further illustrating the effects obtained by the present invention, the results of pharmacological tests of typical compounds of the present invention will be shown below:

Experiments

1. Compounds tested (1) Compound A: 2-[(2,6-dichlorophenyl)amino]phenylacetic acid 3,7,11,15-tetramethyl-2,6,10,14-hexadecatetraenyl ester,
(2) Compound B: 2-(4-isobutylphenyl)propionic acid 3,7,11-trimethyl-2,6,10-dodecatrienyl ester,
(3) Compound C: 1-(p-chlorobenzoyl)-2-methyl-5-methoxy-3-indolylacetic acid 3,7,11-trimethyl-2,6,10-dodecatrienyl ester,
(4) Compound D: 1-(p-chlorobenzoyl)-2-methyl-5-methoxy-3-indolylacetic acid 3,7,11,15-tetramethyl-2,6,10,14-hexadecatetraenyl ester,
(5) Compound E: acetylsalicylic acid 3,7-dimethyl-2,6-octadienyl ester,
(6) Indomethacin, (7) Ibuprofen.

2. Effects of controlling carrageenan-induced edema

Experiment 1

Effects of controlling carrageenan-induced edema were examined by the sole edema method, see Winter et al.; Pro. Soc. Exp. Med., 111, 544 (1962), wherein carrageenan was used as an inflaming agent and male S.D. rats weighing 150-180 g were used as the test animals (each group comprised 5 rats).

As the test compounds, Compound C, Indomethacin and Ibuprofen were used. The test compound was dissoled in sesame oil and the solution was administered perorally to the rats 6 hours before the administration of the inflaming agent. The volumes of the hind leg soles were measured 3 hours after the administration of the inflaming agent. Edema rate was calculated according to the following formula (1) and the edema control rate was calculated according to the following formula (2). The median effective dose ($ED_{50}$) in the carrageenan-induced edema method was calculated from the frequency of cases in which significant edema control was observed (the number of rats having an edema control rate of at least 30%) in each group according to the Litchfield-Wilcoxon method.

$$\text{Edema rate} = \frac{b - a}{a} \times 100 \quad \text{Formula (1)}$$

wherein a is the volume of the hind leg sole before the edema induction and b is the corresponding value after the edema induction.

$$\text{Edema control rate} = \frac{c - d}{c} \times 100 \quad \text{Formula (2)}$$

wherein c represents the average edema rate of the control group and d represents the edema rate of each animal to which the test compound was given.

The results are shown in Table 1.

TABLE 1

| Median effective dose for carrageenan-induced edema | |
|---|---|
| Test compound | $ED_{50}$ (mg/kg) |
| Compound C | 6.5 |
| Indomethacin | 2.9 |
| Ibuprofen | 7.7 |

Experiment 2

Carrageenan-induced edema control rates were determined according to formula (2) in the same manner as in Experiment 1 except that each group comprised 8 rats.

The results are shown in Table 2.

TABLE 2

| Test Compound | Dose (mg/kg) | Control rate (%) |
|---|---|---|
| Compound A | 18 | 34 |
| Compound B | 60 | 30 |
| Compound C | 18 | 42 |
|  | 9 | 40 |
| Compound D | 18 | 22 |
|  | 9 | 22 |
| Compound E | 400 | 52 |
| Indomethacin | 9 | 38 |

3. Effect of controlling adjuvant-induced arthritis

Arthritis was induced in F-344 rats (6 weeks) (Japanese Charles Liver) according to the method of Winder, C. V., et al; Arthritis Rheum. 12, 472-482 (1969) and the controlling effects were examined. 0.05 ml. of a suspension (6 mg/ml) of Mycobacterium butyricum (Difco) in liquid paraffin was injected in the sole of the right leg of each rat to induce arthritis. As test compounds, Compound C and Indomethacin (control) were used. The former was dissolved in sesame oil and the latter was suspended in acacia. The administration of the test compounds was started on the same day as the adjuvant injection. The test compounds were administered perorally every day for 19 days.

Results of examination of median effective doses ($ED_{50}$) for adjuvant-induced arthritis are shown in Table 3.

TABLE 3

| Median effective dose for adjuvant-induced arthritis | |
|---|---|
| Test compound | $ED_{50}$ (mg/kg) |
| Compound C | 3.6 |
| Indomethacin | 1.5 |

It is apparent from the above experimental results that the compounds of the present invention have excellent anti-inflammatory effects.

Toxicities of the compounds of the present invention will be shown below:

Toxicities (1) Acute toxicity

20% solutions of compounds C and D in sesame oil were administered perorally to SD rats and the $LD_{50}$ values were determined by the conventional method.

The results are shown in Table 4.

TABLE 4

| Test compound | $LD_{50}$ (mg/kg) ♂ | $LD_{50}$ (mg/kg) ♀ |
|---|---|---|
| Compound C | 2,000-2,520 | 1,291-1,861 |
| Compound D | 1,533-3,157 | 2,000-2,520 |

It is apparent from Table 4 that the compounds of the present invention have a low toxicity and are quite safe. The above values indicate a far higher safety as compared with Indomethacin which has an $LD_{50}$ of 18 mg/kg.

When compounds C and D of the present invention were administered perorally to SD rats in doses of 50 mg/kg per day and 200 mg/kg per day continuously for one week, no health problem was observed.

(2) Side effects on the stomach and intestines (1) Effects on gastric membranes of normal rats After the rats fasted for 24 hours, 0.5 ml./100 g (body weight) (suspension in 5 wt. % acacia syrup containing 3.6 wt. % Tween 80) of compound C and Indomethacin were administered perorally to Wistar ST rats (7 weeks old). Four hours thereafter, the ulceration conditions in the gastric membranes were examined.

The results are shown in Table 5.

TABLE 5

| Test compound | Dose (mg/kg) | Number of rats | Ulcer index (mean ± S.E.) | Number of ulcerated rats |
|---|---|---|---|---|
| Indomethacin | 20 | 5 | 18.0 ± 3.2 | 5/5 |
| Compound C | 153 | 5 | 0.0 ± 0.0 | 0/5 |

[Molar ratio of dose of compound C (153 mg/kg) to that of Indomethacin was 5:1.]

(2) Worsening of cold restraint stress-induced ulcer

Cold restraint stress was applied to Wistar rats (7 weeks old) by a conventional method. 0.5 ml/100 g (body weight) of compound C or Indomethacin (suspended in 5% acacia syrup containing 3.6% Tween 80) was administered perorally to the rats. Two hours after the application of stress, the length of ulcer (ulcer index) in the gastric membranes was measured.

The results are shown in Table 6.

TABLE 6

| Test compound | Dose (mg/kg) | Number of rats | Ulcer index (Mean ± S.E.) |
|---|---|---|---|
| Control | 0 | 10 | 5.5 ± 1.2 |
| Indomethacin | 20.0 | 10 | 36.5 ± 7.3 |
| Compound C | 30.6 | 10 | 5.6 ± 2.2 |
|  | 153.0 | 10 | 4.9 ± 1.8 |

The following facts are understood from the above experiments on the side effects:

(a) As shown in Table 5, gastric ulcer was not observed at all when the compound of the present invention was given in a molar amount of 5 times as much as that of Indomethacin.

(b) As shown in Table 6, in the group to which Indomethacin was administered, the stress-induced ulcer was increased significantly and linear ulcer accompanied with copious bleeding was clearly recognized by the macroscopic observation. The stress-induced ulcer was not worsened by the compound of the present invention used in a molar amount (153.0 mg/kg) 5 times as much as that of Indomethacin. Thus, it is understood that the compound of the present invention causes less gastroenteric disorders than Indomethacin.

It is concluded from the above results that the compounds of the present invention have excellent, continuous, anti-inflammatory effects and that the most important property thereof is the remarkably reduced side effects on the gastro-intestinal tract, etc. which have been a serious defect of non-steroidal anti-inflammatory drugs used heretofore. In addition, the compounds of the present invention have a far lower toxicity than conventional anti-inflammatory drugs, such as Indomethacin. Thus, the compounds of the present invention are ideal non-steroidal anti-inflammatory drugs. As for the relationship between $LD_{50}$ and $ED_{50}$, compound C of the present invention had an $LD_{50}/ED_{50}$ ratio of 160-230 in the carrageenan-induced edema controlling test and 410-560 in the adjuvant-induced arthritis test, whereas Indomethacin had $LD_{50}/ED_{50}$ ratios of 5-6 and 14-15, respectively.

Thus, it will be apparent that the present invention is of great value.

In using the compounds of the present invention as anti-inflammatory drugs, they are administered perorally or non-perorally (i.e. intramuscular, subcutaneous or intravenous administration or by suppository). The dose varies depending on the symptoms, age and individual differences of patients and is generally about 0.1-500 mg/day, preferably 0.1-100 mg/day for adult human beings.

The compounds of the present invention can be prepared in the form of tablets, granules, powders, capsules, injections, suppositories, etc. by methods generally employed in the art.

In the preparation of a peroral solid product, an excipient and, if necessary, a binder, disintegrator, lubricant, coloring agent and corrigent (flavoring agent) is added to the active ingredient and the mixture is then shaped into tablets, coated tablets, granules, powder or capsules.

As the excipients, there can be used, for example, lactose, corn starch, white sugar, glucose, sorbitol, crystalline cellulose and silicon dioxide. As the binders, there can be used, for example, polyvinyl alcohol, polyvinyl ether, ethylcellulose, methylcellulose, acacia, tragacanth, gelatin, shellac, hydroxypropylcellulose, hydroxypropylstarch, polyvinylpyrrolidone, white sugar and sorbitol. As the disintegrators, there can be used, for example, starch, agar, gelatin powder, crystalline cellulose, calcium carbonate, sodium hydrogencarbonate, calcium citrate, dextrin and pectin. As the lubricants, there can be used, for example, magnesium stearate, talc, polyethylene glycol, silica and hardened vegetable oils. As the colorants, there can be used those allowed as additives to medicines. As the corrigents, there can be used cocoa powder, methanol, aromatic powder, peppermint oil, borneol and cinnamon powder. Those tablets and granules can be coated suitably with sugar, gelatin, etc.

In the preparation of a liquid medicine for peroral administration, a corrigent, buffer, stabilizer, etc. are added, if necessary, to the active ingredient and the mixture is treated to form, for example, a syrup.

In the preparation of an injectable solution, a pH regulator, buffer, suspending agent, solubilizer, stabilizer, isotonizer and preservative are added, if necessary, to the active ingredient and the mixture is treated to form a subcutaneous, intramuscular or intravenous injectable solution.

As the suspending agents, there can be used, for example, methylcellulose, Polysorbate 80, hydroxyethylcellulose, acacia, tragacanth powder, sodium carboxymethylcellulose and polyoxyethylenesorbitan monolaurate. As the solubilizers, there can be used polyoxyethylene-hardened castor oil, Polysorbate 80, nicotinic acid amide, polyoxysorbitan monolaurate, Macrogol, castor oil and fatty acid ethyl esters. As the stabilizers, there can be used, for example, sodium sulfite, sodium metasulfite and ether. As the preservatives, there can be used methyl p-hydroxybenzoate, ethyl p-hydroxybenzoate, sorbic acid, phenol, cresol and chlorocresol.

The present invention will be further described with reference to the following illustrative examples, which by no means limit the present invention.

EXAMPLE 1

1-(p-Chlorobenzoyl)-2-methyl-5-methoxy-3-indolylacetic acid 3,7,11-trimethyl-2,6,10-dodecatrienyl ester A mixture of 12 g of 1-(p-chlorobenzoyl)-2-methyl-5-methoxy-3-indolylacetic acid and 12 g of thionyl chloride was refluxed in 100 ml of benzene for two hours. After cooling, the solvent and excess thionyl chloride were distilled out under reduced pressure and the residue was dissolved in 25 ml of tetrahydrofuran. The resulting solution was added to a solution of 7.6 g of 3,7,11-trimethyl-2,6,10-dodecatrienol (farnesol) and 12 ml of triethylamine in 20 ml of tetrahydrofuran under cooling. After stirring at room temperature for one hour, water was added to the reaction mixture and the product was extracted with n-hexane. The solvent was distilled out under reduced pressure. The oily product was purified by silica gel chromatography [developer: n-hexane/ether (95:5)] to obtain 14 g of 1-(p-chlorobenzoyl)-2-methyl-5-methoxy-3-indolylacetic acid 3,7,11-trimethyl-2,6,10-dodecatrienyl ester as a yellow oil.

(1) Elementary analysis as $C_{34}H_{40}ClNO_4$:

|  | C | H | N |
|---|---|---|---|
| Calcd. (%): | 72.65 | 7.17 | 2.49 |
| Found (%): | 72.64 | 7.16 | 2.50 |

(2) Mass spectrum (m/e): 561
(3) I.R. ($cm^{-1}$): 2970, 2930, 2850, 1728, 1688
(4) N.M.R. ($CDCl_3$):
    7.68 (2H, dd, J = 2Hz, 6.5Hz),
    7.48 (2H, dd, J = 2Hz, 6.5Hz),
    6.98 (1H, d, J = 2Hz)
    6.88 (1H, d, J = 9Hz)
    6.68 (1H, dd, J = 2Hz, 9Hz)
    5.35 (1H, t, J = 6.5Hz)
    5.20 — 4.94 (2H, broad)
    4.63 (2H, d, J = 6.5Hz)
    3.83 (3H, s)
    3.66 (2H, s)
    2.38 (3H, s)
    2.24 — 1.86 (8H, broad)
    1.68 (6H, s)
    1.60 (6H, s)

EXAMPLE 2

1-(p-Chlorobenzoyl)-2-methyl-5-methoxy-3-indolylacetic acid 3,7,11,15-tetramethyl-2,6,10,14-hexadecatetraenyl ester A mixture of 12 g of 1-(p-chlorobenzoyl)-2-methyl-5-methoxy-3-indolylacetic acid and 12 g of thionyl chloride was refluxed in 100 ml of benzene for two hours. After cooling, the solvent and excess thionyl chloride were distilled out under reduced pressure and the residue was dissolved in 25 ml of tetrahydrofuran. The resulting solution was added dropwise to a solution of 9.9 g of 3,7,11,15-tetramethyl-2,6,10,14-hexadecatetraenol (geranylgeraniol) and 12 ml of triethylamine in 20 ml of tetrahydrofuran under cooling. After stirring at room temperature for one hour, water was added to the reaction mixture and the product was extracted with n-hexane. The solvent was distilled out under reduced pressure. The oily product was purified by silica gel chromatography [developer: n-hexane/ether (95:5)] to obtain 16 g of 1-(p-chlorobenzoyl)-2-methyl-5-methoxy-3-indolylacetic acid 3,7,11,15-tetramethyl-2,6,10,14-hexadecatetraenyl ester as a yellow oil.

(1) Elementary analysis as $C_{39}H_{48}ClNO_4$:

|  | C | H | N |
|---|---|---|---|
| Calcd. (%): | 74.32 | 7.68 | 2.22 |
| Found (%): | 74.30 | 7.69 | 2.21 |

(2) Mass spectrum (m/e): 629
(3) I.R. ($cm^{-1}$): 2970, 2930, 2850, 1725, 1685
(4) N.M.R. ($CDCl_3$):
    7.68 (2H, dd, J = 2Hz, 8.8Hz)
    7.46 (2H, dd, J = 2Hz, 8.8Hz)
    6.97 (1H, d, J = 2Hz)
    6.86 (1H, d, J = 9Hz)
    6.66 (1H, dd, J = 2Hz, 9Hz)
    5.36 (1H, t, J = 7Hz)
    5.24 — 4.92 (3H, broad)
    4.63 (2H, d, J = 7Hz)
    3.83 (3H, s)
    3.66 (2H, s)
    2.37 (3H, s)
    2.20 — 1.84 (12H, broad)
    1.68 (6H, s)
    1.60 (9H, s)

EXAMPLE 3

1-(p-Chlorobenzoyl)-2-methyl-5-methoxy-3-indolylacetic acid 3,7-dimethyl-2,6-octadienyl ester The intended compound having the following properties was obtained in the same manner as in Example 1:

(1) Elementary alalysis as $C_{29}H_{32}ClNO_4$:

|  | C | H | N |
|---|---|---|---|
| Calcd. (%): | 70.51 | 6.53 | 2.84 |
| Found (%): | 70.53 | 6.53 | 2.85 |

(2) Mass spectrum (m/e): 493
(3) I.R. ($cm^{-1}$): 2970, 2930, 2850, 1730, 1685
(4) N.M.R. ($CDCl_3$) δ:
    7.68 (2H, J = 2Hz, 6.5Hz)
    7.47 (2H, dd, J = 2Hz, 6.5Hz)
    6.97 (1H, d, J = 2Hz)
    6.88 (1H, d, J = 9Hz)
    6.67 (1H, dd, J = 2Hz, 9Hz)
    5.35 (1H, t, J = 6.5Hz)
    5.18 — 4.92 (1H, broad)
    4.62 (2H, d, J = 6.5Hz)
    3.82 (3H, s)
    3.66 (2H, s)
    2.38 (3H, s)
    2.23 — 1.84 (4H, broad)
    1.67 (3H, s)
    1.59 (6H, s)

EXAMPLE 4

Acetylsalicylic acid 3,7-dimethyl-2,6-octadienyl ester 7 g of 3,5-dimethyl-2,6-octadienol (geraniol) and 6.8 g of triethylamine were dissolved in 50 ml of tetrahydrofuran. 13.4 g of acetylsalicylic acid chloride was added dropwise to the solution under cooling. After stirring at room temperature for 30 minutes, water was added to the reaction mixture and the product was extracted with n-hexane.

The solvent was distilled out under reduced pressure. The resulting oily product was purified by silica gel column chromatography [developer: n-hexane/benzene (1:1)] to obtain 6 g of acetylsalicylic acid 3,5-dimethyl-2,6-octadienyl ester as a colorless oil.

(1) Elementary analysis as $C_{19}H_{24}O_4$:

|  | C | H |
|---|---|---|
| Calcd. (%): | 72.12 | 7.65 |
| Found (%): | 72.13 | 7.63 |

(2) Mass spectrum (m/e): 316
(3) I.R. ($cm^{-1}$): 2970, 2930, 2850, 1770, 1718
(4) N.M.R. ($CDCl_3$):
    8.02 (1H, dd, J = 2Hz, 7Hz)
    7.67 (1H, dt, J = 2Hz, 7Hz)
    7.28 (1H, dt, J = 2Hz, 8Hz)
    7.08 (1H, dd, J = 2Hz, 8Hz)
    5.44 (1H, t, J = 7Hz)
    5.22 — 4.96 (1H, broad)
    4.78 (2H, d, J = 7Hz)
    2.32 (3H, s)
    2.22 — 18.0 (4H, broad)
    1.74 (3H, s)
    1.67 (6H, s)

-continued 1.58 (6H, s)

EXAMPLE 5

Acetylsalicylic acid 3,7,11-trimethyl-2,6,10-dodecatrienyl ester

The intended compound having the following physical properties was obtained in the same manner as described in Example 4:

(1) Elementary analysis as $C_{24}H_{32}O_4$:

|  | C | H |
| --- | --- | --- |
| Calcd. (%): | 74.97 | 8.39 |
| Found (%): | 74.96 | 8.40 |

(2) Mass spectrum (m/e): 384
(3) I.R. (cm$^{-1}$): 2970, 2930, 2850, 1770, 1718
(4) N.M.R. (CDCl$_3$) δ:
   8.02 (1H, dd, J = 2Hz, 7Hz)
   7.68 (1H, dt, J = 2Hz, 7Hz)
   7.28 (1H, dt, J = 2Hz, 8Hz)
   7.08 (1H, dd, J = 2Hz, 8Hz)
   5.44 (1H, t, J = 7Hz)
   5.20 − 4.95 (2H, broad)
   4.78 (2H, d, J = 7Hz)
   2.30 (3H, s)
   2.20 − 1.82 (8H, broad)
   1.73 (3H, s)
   1.66 (3H, s)
   1.58 (6H, s)

EXAMPLE 6

Acetylsalicylic acid 3,7,11,15-tetramethyl-2,6,10,14-hexadecatetraenyl ester

The intended compound having the following physical properties was obtained in the same manner as described in Example 4:

(1) Elementary analysis as $C_{29}H_{40}O_4$:

|  | C | H |
| --- | --- | --- |
| Calcd. (%): | 76.95 | 8.91 |
| Found (%): | 76.95 | 8.92 |

(2) Mass spectrum (m/e): 452
(3) I.R. (cm$^{-1}$): 2970, 2930, 2850, 1770, 1718
(4) N.M.R. (CDCl$_3$) δ:
   8.01 (1H, dd, J = 2Hz, 7Hz)
   7.66 (1H, dt, J = 2Hz, 7Hz)
   7.28 (1H, dt, J = 2Hz, 8Hz)
   7.07 (1H, dd, J = 2Hz, 8Hz)
   5.43 (1H, t, J = 7Hz)
   5.20 − 4.96 (3H, broad)
   4.77 (2H, d, J = 7Hz)
   2.32 (3H, s)
   2.20 − 1.82 (12H, broad)
   1.73 (3H, s)
   1.66 (3H, s)
   1.58 (3H, s)

EXAMPLE 7

2-(4-Isobutylphenyl)propionic acid 3,7,11-trimethyl-2,6,10-dodecatrienyl ester 1.1 g of sodium hydride (55% dispersion in oil) was dispersed in 30 ml of hexamethylphosphoramide. 5 g of 2-(4-isobutylphenyl)propionic acid was added in portions to the dispersion under cooling. After stirring at room temperature for 30 minutes, a solution of 7 g of 3,7,11-trimethyl-2,6,10-dodecatrienyl bromide (farnesyl bromide) in 20 ml of tetrahydrofuran was added dropwise to the mixture. After stirring for one hour, water was added to the reaction mixture and the product was extracted with n-hexane.

The solvent was distilled out under reduced pressure. The resulting oily product was purified by silica gel column chromatography [developer: n-hexane/benzene (8:2)] to obtain 4 g of 2-(4-isobutylphenyl)propionic acid 3,7,11-trimethyl-2,6,10-dodecatrienyl ester as a colorless oil.

(1) Elementary analysis as $C_{28}H_{42}O_2$:

|  | C | H |
| --- | --- | --- |
| Calcd. (%): | 81.91 | 10.31 |
| Found (%): | 81.91 | 10.31 |

(2) Mass spectrum (m/e): 410
(3) I.R. (cm$^{-1}$): 2950, 2920, 2870, 1725
(4) N.M.R. (CDCl$_3$) δ:
   7.23 (2H, d, J = 8Hz)
   7.08 (2H, d, J = 8Hz)
   5.29 (1H, t, J = 6.5Hz)
   5.18 − 4.96 (2H, broad)
   4.57 (2H, d, J = 6.5Hz)
   3.68 (1H, q, J = 7Hz)
   2.44 (2H, d, J = 7Hz)
   2.24 − 1.80 (8H, broad)
   1.96 − 1.76 (1H, m)
   1.68 (3H, s)
   1.64 (3H, s)
   1.60 (6H, s)
   1.47 (3H, d, J = 7Hz)
   0.88 (6H, d, J = 6Hz)

EXAMPLE 8

2-(4-Isobutylphenyl)propionic acid 3,7-dimethyl-2,6-octadienyl ester

The intended compound having the following physical properties was obtained in the same manner as described in Example 7:

(1) Elementary analysis as $C_{23}H_{34}O_2$:

|  | C | H |
| --- | --- | --- |
| Calcd. (%): | 80.65 | 10.01 |
| Found (%): | 80.66 | 10.02 |

(2) Mass spectrum (m/e): 342
(3) I.R. (cm$^{-1}$): 2950, 2920, 2870, 1725
(4) N.M.R. CDCl$_3$ δ:
   7.24 (2H, d, J = 8Hz)
   7.10 (2H, d, J = 8Hz)
   5.31 (1H, t, J = 6.5Hz)
   5.20 −4.98 (1H, broad)
   4.58 (2H, d, J = 6.5Hz)
   3.70 (1H, q. J = 7Hz)
   2.45 (2H, d, J = 7Hz)
   2.28 − 1.82 (4H, broad)
   1.98 − 1.76 (1H, m)
   1.69 (3H, s)
   1.66 (3H, s)
   1.62 (3H, s)
   1.48 (3H, d, J = 7Hz)
   0.89 (6H, d, J = 6Hz)

EXAMPLE 9

2-(4-Isobutylphenyl)propionic acid 3,7,11,15-tetramethyl-2,6,10,14-hexadecatetraenyl ester The intended compound having the following physical properties were obtained in the same manner as described in Example 7:

(1) Elementary analysis as $C_{33}H_{50}O_2$:

|  | C | H |
| --- | --- | --- |
| Calcd. (%): | 82.79 | 10.53 |
| Found (%): | 82.80 | 10.54 |

-continued (2) Mass spectrum (m/e): 478
(3) I.R. (cm$^{-1}$): 2950, 2926, 2870, 1725
(4) N.M.R. (CDCl$_3$) δ:
7.22 (2H, d, J = 8Hz)
7.08 (2H, d, J = 8Hz)
5.28 (1H, t, J = 6.5Hz)
5.17 − 4.95 (3H, broad)
4.57 (2H, d, J = 6.5Hz)
3.67 (1H, q, J = 7Hz)
2.42 (2H, d, J = 7Hz)
2.24 − 1.78 (12H, broad)
1.95 − 1.784 (1H, m)
1.67 (3H, s)
1.63 (6H, s)
1.59 (6H, s)
1.46 (3H, d, J = 7Hz)
0.88 (6H, d, J = 6Hz)

EXAMPLE 10

2-[(2,6-Dichlorophenyl)amino]phenylacetic acid 3,7,11,15-tetramethyl-2,6,10,14-hexadecatetraenyl ester 0.24 g of sodium hydride (55% dispersion in oil) was dispersed in 10 ml of hexamethylphosphoramide. 2.7 g of 2-[(2,6-dichlorophenyl)amino]phenylacetic acid was added in portions to the dispersion under cooling. After stirring at room temperature for 30 minutes, a solution of 3.5 g of 3,7,11,15-tetramethyl-2,6,10,14-hexadecatetraenyl bromide in 20 ml of tetrahydrofuran was added dropwise to the reaction mixture. After stirring for one hour, water was added to the reaction mixture and the product was extracted with n-hexane.

The solvent was distilled out under reduced pressure. The resulting oily product was purified by silica gel column chromatography [developer: n-hexane/benzene (7:3)] to obtain 3 g of 2-[(2,6-dichlorophenyl)amino]phenylacetic acid 3,7,11,15-tetramethyl-2,6,10,14-hexadecatetraenyl ester as a colorless oil.

(1) Elementary analysis as C$_{34}$H$_{43}$Cl$_2$NO$_2$:

|  | C | H | N |
|---|---|---|---|
| Calcd. (%): | 71.82 | 7.62 | 2.46 |
| Found (%): | 71.80 | 7.61 | 2.48 |

(2) Mass spectrum (m/e): 567
(3) I.R. (cm$^{-1}$): 3300, 2960, 2920, 2840, 1710
(4) N.M.R. (CDCl$_3$) δ:
7.30 (2H, d, J = 8Hz)
7.30 − 6.78 (5H, m)
6.51 (1H, d, J = 8Hz)
5.33 (1H, t, J = 7Hz)
5.16 − 4.92 (3H, broad)
4.63 (2H, d, J = 7Hz)
3.75 (2H, s)
2.26 − 1.75 (12H, broad)
1.67 (6H, s)
1.60 (9H, s)

EXAMPLE 11

2-[(2,6-Dichlorophenyl)amino]phenylacetic acid 3,7-dimethyl-2,6-octadienyl ester The intended compound having the following physical properties was obtained in the same manner as described in Example 10:

(1) Elementary analysis as C$_{24}$H$_{27}$Cl$_2$NO$_2$:

|  | C | H | N |
|---|---|---|---|
| Calcd. (%): | 66.67 | 6.29 | 3.24 |
| Found (%): | 66.66 | 6.29 | 3.23 |

(2) Mass spectrum (m/e): 431
(3) I.R. (cm$^{-1}$): 3300, 2960, 2920, 2840, 1710
(4) N.M.R. (CDCl$_3$) δ:
7.30 (2H, d, J = 8Hz)
7.29 − 6.79 (5H, m)
6.51 (1H, d, J = 8Hz)
5.32 (1H, t, J = 7Hz)
5.19 − 4.92 (1H, broad)
4.64 (2H, d, J = 7Hz)
3.75 (2H, s)
2.24 − 1.77 (4H, broad)
1.66 (3H, s)
1.56 (6H, s)

EXAMPLE 12

2-[(2,6-Dichlorophenyl)amino]phenylacetic acid 3,7,11-trimethyl-2,6,10-dodecatrienyl ester The intended compound having the following physical properties was obtained in the same manner as described in Example 10:

(1) Elementary analysis as C$_{29}$H$_{35}$Cl$_2$NO$_2$:

|  | C | H | N |
|---|---|---|---|
| Calcd. (%): | 69.58 | 7.05 | 2.80 |
| Found (%): | 69.56 | 7.04 | 2.81 |

(2) Mass spectrum (m/e): 499
(3) I.R. (cm$^{-1}$): 3300, 2960, 2920, 2840, 1710
(4) N.M.R. (CDCl$_3$) δ:
7.32 (2H, d, J = 8Hz)
7.30 − 6.80 (5H, m)
6.52 (1H, d, J = 8Hz)
5.33 (1H, t, J = 7Hz)
5.18 − 4.93 (2H, broad)
4.64 (2H, d, J = 7Hz)
3.76 (2H, s)
2.24 − 1.76 (8H, broad)
1.66 (6H, s)
1.56 (6H, s)

We claim:

1. A compound having the formula:

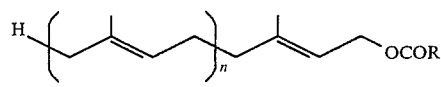

wherein R is a group having the formula:

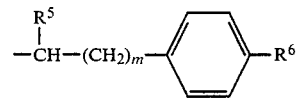

in which $R^5$ represents lower alkyl, $R^6$ represents lower alkyl, m represents the integer of 0 or 1, and n represents an integer of 2 or 3.

2. A compound according to claim 1 which is 2-(4-isobutylphenyl)propionic acid 3,7,11-trimethyl-2,6,10-dodecatrienyl ester.

3. A compound according to claim 1 which is 2-(4-isobutylphenyl)propionic acid 3,7,11,15-tetramethyl-2,6,10,14-hexadecatetraenyl ester.

4. An anti-inflammatory composition containing, as an active ingredient, a therapeutically effective amount of a compound as claimed in claim 1, in combination with a pharmacologically acceptable carrier, diluent or vehicle.

5. A method for treating a patient suffering from an inflammatory disease which comprises administering to said patient a composition as claimed in claim 4.

6. A method for treating a patient suffering from rheumatism or arthritis which comprises administering to said patient a composition containing a therapeutically effective amount of compound having the formula:

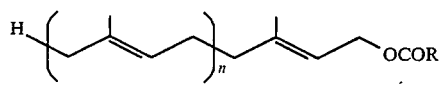

wherein R is a group having the formula:

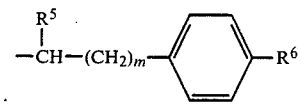

in which $R^5$ represents hydrogen or lower alkyl, $R^6$ represents lower alkyl, m represents an integer of 0 or 1 and n represents an integer of 1 to 3, in combination with a pharmacologically acceptable carrier, diluent or vehicle.

* * * * *